United States Patent
Takada et al.

(10) Patent No.: US 8,158,145 B2
(45) Date of Patent: *Apr. 17, 2012

(54) PERCUTANEOUS ABSORPTION TYPE PLASTER

(75) Inventors: Yasunori Takada, Tosu (JP); Koji Tanaka, Tosu (JP); Yasuhiro Ikeura, Tosu (JP)

(73) Assignee: Hisamitsu Pharmaceutical Co., Inc., Tosu-shi, Saga (JP)

( * ) Notice: Subject to any disclaimer, the term of this patent is extended or adjusted under 35 U.S.C. 154(b) by 1053 days.

This patent is subject to a terminal disclaimer.

(21) Appl. No.: 10/504,872

(22) PCT Filed: Feb. 19, 2003

(86) PCT No.: PCT/JP03/01805
§ 371 (c)(1),
(2), (4) Date: Jan. 12, 2005

(87) PCT Pub. No.: WO03/070228
PCT Pub. Date: Aug. 28, 2003

(65) Prior Publication Data
US 2005/0129748 A1    Jun. 16, 2005

(30) Foreign Application Priority Data
Feb. 19, 2002 (JP) ............................. P2002-042037

(51) Int. Cl.
*A61K 31/192*    (2006.01)
*A61K 9/70*      (2006.01)

(52) U.S. Cl. ........................................................ 424/449

(58) Field of Classification Search .................... 424/449
See application file for complete search history.

(56) References Cited

U.S. PATENT DOCUMENTS

| | | | |
|---|---|---|---|
| 4,421,737 A | 12/1983 | Ito et al. | |
| 4,695,465 A * | 9/1987 | Kigasawa et al. | 424/449 |
| 5,208,035 A | 5/1993 | Okuyama et al. | |
| 5,776,484 A * | 7/1998 | Sasaki et al. | 424/448 |
| 5,945,125 A * | 8/1999 | Kim | 424/473 |
| 6,262,121 B1* | 7/2001 | Kawaji et al. | 514/567 |
| 6,616,941 B1* | 9/2003 | Seo et al. | 424/450 |
| 2002/0106401 A1* | 8/2002 | Hori et al. | 424/448 |

FOREIGN PATENT DOCUMENTS

| | | |
|---|---|---|
| CA | 1 144-070 | 4/1983 |
| CA | 2 200 068 C | 3/1996 |
| EP | 0 524 582 A1 | 1/1993 |
| EP | 0 997 144 A1 | 5/2000 |

(Continued)

OTHER PUBLICATIONS

Machine Translation of Kawakami et al (JP 2001-302502).*

(Continued)

*Primary Examiner* — Sharmila G. Landau
*Assistant Examiner* — Rachael E Bredefeld
(74) *Attorney, Agent, or Firm* — The Nath Law Group

(57) ABSTRACT

A transdermal patch comprising a backing 2 and an adhesive layer 3 laminated on the backing 2, wherein the adhesive layer 3 comprises a rosin-based resin and petroleum resin as a tackifier, the total compounding amount of the rosin-based resin and the petroleum resin is in a range of 15% by mass to 50% by mass, and compounding amount of the petroleum resin is $\frac{1}{3}$ times by mass to 4 times by mass as that of the rosin-based resin.

4 Claims, 3 Drawing Sheets

FOREIGN PATENT DOCUMENTS

| | | |
|---|---|---|
| GB | 2 045 618 A | 11/1980 |
| GB | 2 073 588 A | 10/1981 |
| GB | 2073588 A | 10/1981 |
| JP | 61-233077 | 10/1986 |
| JP | 61-233077 A | 10/1986 |
| JP | 63246326 A | 10/1988 |
| JP | 4103528 A | 4/1992 |
| JP | 5155762 A | 6/1993 |
| JP | 05-201879 | 8/1993 |
| JP | 5-201879 A | 8/1993 |
| JP | 6024969 A | 2/1994 |
| JP | 08-026985 | 1/1996 |
| JP | 8-26985 A | 1/1996 |
| JP | 8-026985 A | 1/1996 |
| JP | 09-208460 | 8/1997 |
| JP | 9-208460 A | 8/1997 |
| JP | 9315957 A | 12/1997 |
| JP | 10-182450 | 7/1998 |
| JP | 10-182450 A | 7/1998 |
| JP | 10218793 A | 8/1998 |
| JP | 2816765 | 10/1998 |
| JP | 11035458 A | 2/1999 |
| JP | 11 255644 | 9/1999 |
| JP | 11-255644 A | 9/1999 |
| JP | 2001-058961 | 3/2001 |
| JP | 2001-058961 A | 3/2001 |
| JP | 2001-58961 A | 3/2001 |
| JP | 2001302502 A | 10/2001 |
| KR | 2000-0068581 | 11/2000 |
| WO | 99/54422 A1 | 10/1999 |

OTHER PUBLICATIONS

"Adhesive compsn. For low polar plastic resins-comprises an alkyl(meth)acrylate copolymer, and tackifier comprising rosin and hydrogenated petroleum resin", DERWENT, Jan. 27, 1995, XP002216523, two pages.

Supplementary European Search Report under Article 153(7) EPC, mailed on Aug. 16, 2010, five pages.

* cited by examiner ized the transdermal patch comprising a
PERCUTANEOUS ABSORPTION TYPE PLASTER

CROSS-REFERENCED APPLICATIONS

This application is the U.S. National Stage of International Application PCT/JP03/01805, filed Feb. 19, 2003, the complete disclosure of which is incorporated herein by reference, which International Application designated the U.S. and was not published under PCT Article 21(2) in English.

TECHNICAL FIELD

This invention relates to a transdermal patch comprising a backing and an adhesive layer laminated thereon.

BACKGROUND ART

Concerning an anti-inflammatory agent such as ketoprofen, in order to be absorbed through the skin, many kinds of transdermal patch are known, and a patch using an adhesive base agent including a thermoplastic elastomer such as natural rubber, acrylate polymers, and styrene-isoprene-styrene blocka copolymers is known. In Japanese Patent No. 2816765, for example, a patch having an adhesive layer consisting of styrene-isoprene-styrene block copolymer as an adhesive base agent (base polymer), a rosin ester derivative as a tackifier, L-menthol as a solubilizer, liquid paraffin as a plasticizer, and an anti-inflammatory agent such as ketoprofen.

However, for conventional anti-inflammatory analgesic patch described in Japanese Patent No. 2816765, in order to provide a temporal stability in its sufficient adhesibility, increase of a compounding amount of rosin ester derivatives is required. However, this increase brings about a problem such that releasability of a medicine is reduced. The problem is prominent when a medicine such as diclofenac or a salt thereof which has generally difficulty in satisfying both of solubility and releasability is used as the medicine.

DISCLOSURE OF INVENTION

The present invention was achieved in consideration of the problems included in the conventional technique, and the object of the invention is to provide a transdermal patch that, even in the case where a medicine such as diclofenac or a salt thereof which generally has difficulty in satisfying both of sufficient solubility and releasability is used as the medicine, both of sufficient solubility and releasability of the medicine are achieved in a high degree with a good balance, and that the temporal stability thereof in adhesive force is also superior.

The present inventors made efforts to achieve the aforementioned object, and found that the object is achieved by incorporating a rosin-based resin and a petroleum resin at a prescribed compounding ratio as a tackifier in the adhesive layer, to reach the invention.

In other words, the transdermal patch of the invention is characterized in being a transdermal patch having a backing and an adhesive layer laminated on the backing, wherein the adhesive layer comprises a rosin-based resin and petroleum resin as a tackifier, the total compounding amount of the rosin-based resin and the petroleum resin is in a range of 15% by mass to 50% by mass, and the compounding amount of the petroleum resin is $1/3$ times by mass to 4 times by mass as that of the rosin-based resin.

It is preferable for the transdermal patch of the invention that the rosin-based resin is a hydrogenated rosin ester, and that the petroleum resin is an alicyclic petroleum resin or a hydrogenated alicyclic petroleum resin.

Preferably, the transdermal patch of the invention comprises one or more selected from the group consisting of diclofenac and a pharmaceutically acceptable salt thereof in the adhesive layer as a medicine.

Moreover, preferably the transdermal patch of the invention further comprises L-menthol and/or polyethylene glycol in the adhesive layer. Regarding such polyethylene glycol, a polyethylene glycol having an average molecular weight in a range from 200 to 20,000 is more preferable.

BEST MODE FOR CARRYING OUT THE INVENTION

Figure 1:
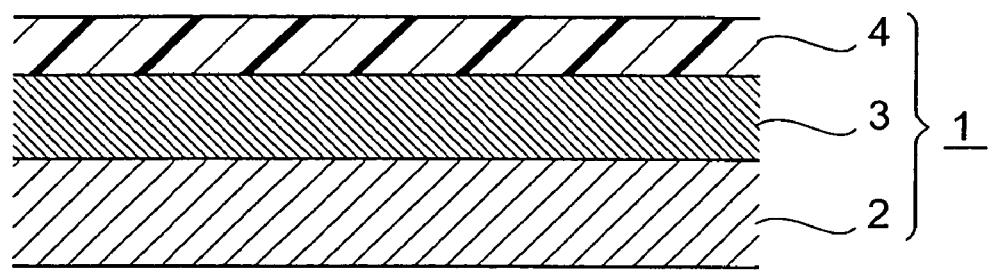
FIG. 1 is a schematic cross-sectional view showing a preferable embodiment of the transdermal patch of the invention.

FIG. 1 is a schematic cross-sectional view showing a preferable embodiment of the transdermal patch of the invention. The transdermal patch 1 of the invention is a transdermal patch comprising a backing 2 and an adhesive layer (pressure-sensitive adhesive layer) 3 laminated on the backing 2, which may be further laminated with a release film 4 that is peeled off when used. In addition, the adhesive layer 3 comprises a rosin-based resin and a petroleum resin as a tackifier.

First, the adhesive layer of the transdermal patch according to the invention will be explained. The adhesive layer according to the invention comprises an adhesive base agent and a tackifier and, if necessary, a medicine. Examples of the adhesive base agent according to the invention include styrene-isoprene-styrene block copolymer, styrene-butadiene-styrene block copolymer, styrene-isoprene rubber, styrene-butadiene rubber, polyisoprene, polyisobutylene, polybutadiene rubber, silicone rubber, acrylate polymer (a copolymer of at least two species of butyl acrylate, 2-ethylhexyl acrylate, vinyl acetate, methacrylate, hydroxyethyl acrylate, glycidyl methacrylate, methoxyethyl acrylate and acrylic acid), natural rubber and polyurethane-based rubbers. Among them, from the viewpoint of cohesive property, weather resistance, aging resistance or chemical resistance, styrene-isoprene-styrene block copolymer and polyisobutylene are preferable, and a mixture of styrene-isoprene-styrene block copolymer and polyisobutylene is especially preferable.

Examples of such styrene-isoprene-styrene block copolymer include Califlex TR-1107, TR-1111, TR-1112, TR-1117 (trade name, Shell Chemicals), Quintac 3530, 3421, 3570C (trade name, ZEON CORPORATION), JSR SIS-5000, 5002 (trade name, Japan Synthetic Rubber Co., Ltd.), Kraton D-KX401CS, D-1107CU (trade name, Shell Chemicals), Solprene 428 (trade name, Phillips Petroleum), which may be used individually or in combination of two or more of them. The compounding amount of the styrene-isoprene-styrene block copolymer is preferably 5-40% by mass of the whole amount of the adhesive layer (adhesive formulation), more preferably 10-35% by mass. The compounding amount lower than the lowest limit described above tends to reduce the cohesive property or shape preservation property of the base agent and, on the other hand, the compounding amount higher than the highest limit described above tends to increase cohesive power of the base agent to reduce easily adhesibility, processability or the like.

Examples of polyisobutylene include Oppanol B-3, B-10, B-15, B-50, B-100, B-200 (trade name, BASF Ltd.), Vistanex LM-MS, LM-MH, MML-80, LLM-100, LLM-120, LLM-140 (trade name, Exxon Chemical Company) and Tetrax 3T, 4T, 5T, 6T (trade name, NIPPON PETROCHEMICALS COMPANY, LIMITED), which may be used individually or in combination of two or more of them. The compounding amount of the polyisobutylene is preferably 1-25% by mass of the whole amount of the adhesive layer (adhesive formulation), more preferably 2-20% by mass. The compounding amount lower than the lowest limit described above tends to reduce adhesibility of the base agent and, on the other hand, the compounding amount higher than the highest limit described above tends to reduce the shape preservation property of the base agent during long preservation.

The adhesive layer according to the invention comprises a rosin-based resin and a petroleum resin as a tackifier along with the adhesive base agent described above. Examples of the rosin-based resin include natural resin rosin, denatured rosin, rosin esters (such as rosin glycerin ester and rosin pentaerythritol ester), hydrogenated rosin esters (such as hydrogenated rosin glycerin ester and hydrogenated rosin pentaerythritol ester). Among them, from the viewpoint of skin irritation and aging resistance, hydrogenated rosin ester is preferable, and hydrogenated rosin glycerin ester is especially preferable. Specifically, examples of such rosin-based resin include Ester gum H (trade name, ARAKAWA CHEMICAL INDUSTRIES LTD.), Pinecrystal KE-100, KE-311 (trade name, ARAKAWA CHEMICAL INDUSTRIES LTD.), Foral 85, 105 (trade name, RIKA-Hercules Inc.) and Stebelite Ester 7, 10 (trade name, RIKA-Hercules Inc.), which can be used individually or in combination of two or more of them.

Examples of the petroleum resin include CS synthesized petroleum resins (copolymers of at least two of isoprene, cyclopentadiene, 1,3-pentadiene and 1-pentene; copolymers of at least two of 2-pentene and dicyclopentadiene; resins mainly composed of 1,3-pentadiene, and the like), C9 synthesized petroleum resins (copolymers of at least two of indene, styrene, methylindene, α-methylstyrene, and the like), dicyclopentadiene-based synthesized petroleum resins (copolymer mainly composed of dicyclopentadiene with isoprene and/or with 1,3-pentadiene, and the like). C9 synthesized petroleum resins are preferable from the viewpoint of weather resistance and miscibility with the adhesive base agent. Also, from the view point of another classification, the petroleum resin includes alicyclic petroleum resins (alicyclic hydrocarbon resins), hydrogenated alicyclic petroleum resins, aliphatic petroleum resins (aliphatic hydrocarbon resins), hydrogenated aliphatic petroleum resins, aromatic petroleum resins and the like. From the viewpoint of adhesive force, miscibility with an adhesive base agent and aging resistance, alicyclic petroleum resins and hydrogenated alicyclic petroleum resins are preferable, and hydrogenated alicyclic petroleum resins are especially preferable. Specific examples of such petroleum resin include ARKON P-70, ARKON P-90, ARKON P-100, ARKON p-115, ARKON P-125 (trade name, ARAKAWA CHEMICAL INDUSTRIES LTD.), Escorez 8000 (trade name, ESSO Petroleum Co., Ltd.), which may be used individually or in combination of two or more of them.

In the adhesive layer according to the invention, the total compounding amount of the rosin-based resin and the petroleum resin is 15% by mass to 50% by mass, preferably 20% by mass to 45% by mass. The total compounding amount lower than the lowest limit described above tends not to give sufficient adhesibility that makes a long-term attaching possible and, on the other hand, that higher than the highest limit described above tends to bring about decrease of medicine release, pain at peeling, or generate easily skin rash. Further, in the adhesive layer according to the invention, the compounding amount of the petroleum resin is ⅓ times by mass to 4 times by mass as the compounding amount of the rosin-based resin, preferably ⅔ times by mass to 3 times by mass. A ratio lower than the lowest limit described above deteriorates releasability of a medicine and generates reduction of the adhesive force over time due to penetration of an adhesive agent (applicator) into the backing during preservation because of a small cohesion force of the resin. On the other hand, a ratio higher than the highest limit described above deteriorates miscibility with a medicine to generate crystallization of the medicine.

In this connection, the adhesive layer according to the invention may further comprise another kind of tackifier (such as terpene-based resin, phenol-based resin and xylene-based resin) in addition to the aforementioned rosin-based resin and petroleum resin.

The adhesive layer according to the invention preferably comprises a medicine if necessary, in addition to the adhesive base agent and tackifier described above. The medicine applicable to the invention is not limited insofar as it is a medicine absorbed transdermally, for example, includes an anti-inflammatory agent, muscle relaxant, cardiac stimulant, therapeutic agent for circulatory organ and anti-allergy agent. Among them, an anti-inflammatory agent selected from the group consisting of salicylic acid, sulpyrine, amfenac, diclofenac, loxoprofen, tolmetin, lobenzarit, ketorolac, ketoprofen, ibuprofen, felbinac, flurbiprofen, indomethacin, zomerac, flufenamic acid, fenoprofen, bromfenac, hydrocortisone succinate, hydrocortisone phosphate, dexamethasone phosphate, dexamethasone m-sulfobenzoate, betamethasone phosphate, prednisolone succinate, prednisolone phosphate, methylprednisolone succinate, prasterone sulfate, ketotifen, oxybutynin, fentanyl, pergolide and a pharmaceutically acceptable salt thereof is preferable. The transdermal patch of the invention allows to satisfy easily both of solubility and releasability of the medicine, thus it is particularly preferable to apply diclofenac or a pharmaceutically acceptable salt thereof, which was conventionally difficult in satisfying both of solubility and releasability.

Examples of a pharmaceutically acceptable salt of the medicine include alkali metal compounds, alkali earth metal compounds and ammonium compounds and, specifically, sodium, potassium, calcium, magnesium, ammonia, dimethylamine, diethylamine, trimethylamine, tetramethyl ammonium, monoethanolamine, diethanolamine and triethanolamine.

The compounding amount of the medicine in the adhesive layer according to the invention is not limited insofar as a pharmaceutical effect is exerted. Generally, it is 0.1-40% by mass, preferably 0.5-30% by mass. The medicine may be used individually or in combination of two or more kinds.

In the case where a compounding medicine is an acidic medicine such as diclofenac or a pharmaceutically acceptable salt thereof, it is preferable that the adhesive layer further comprises an adduct of basic substance. "An adduct of basic substance" refers to a compound of a basic substance added with another substance to form a salt. Preferably, the basic substance is Lewis base, and the other substance is a substance having an electron deficient system such as Lewis acid or a substance that can form an electron deficient system such as an organic halide. The adduct of a basic substance includes specifically salts of ammonium compounds, and preferably acid adducts of ammonia such as ammonium chloride and acid adducts of amines such as diethylamine hydrochloride. When an adduct of a basic substance is added, its cationic moieties are ion-exchanged by or form complex ionic substances with a part or whole of the cationic moieties of an acidic medicine, and the ion-exchanged body or complex ionic substance formed as the result tends to improve a transdermal absorption property.

The compounding amount of the adduct of a basic substance in the adhesive layer according to the invention may be an amount sufficient to form an ion pair with an acidic medicine and, generally, preferably within a range of 0.5-10 times by mol the acidic medicine. The adduct of a basic substance may be used individually or in combination of two or more kinds.

In the patch of the invention, the adhesive layer may further comprise an organic acid. Examples of such organic acid include aliphatic (mono, di, tri) carboxylic acids (acetic acid, propionic acid, isobutyric acid, caproic acid, caprylic acid, lactic acid, maleic acid, pyruvic acid, oxalic acid, succinic acid, tartaric acid, and the like), aromatic carboxylic acids (phthalic acid, salicylic acid, benzoic acid, acetyl salicylic acid, and the like), alkyl sulfonic acids (methane sulfonic acid, ethane sulfonic acid, propyl sulfonic acid, butane sulfonic acid, polyoxyethylenealkylether sulfonic acid, and the like), alkyl sulfonic acid derivatives (N-2-hydroxyethylpiperidine-N'-2-ethane sulfonic acid, and the like) and cholic acid derivatives (dehydrocholic acid, and the like). Among them, monocarboxylic acids or alkyl sulfonic acids are preferable, and especially, acetic acid is preferable. These organic acids may be used in the form of salts thereof or a mixture of the organic acid and the salt thereof.

The organic acid and/or the salt thereof is arbitrarily compounded preferably in a range of 0.01-20% by mass, more preferably 0.1-15% by mass, and especially preferably 0.1-10% by mass based on the total mass of the composition consisting of the adhesive layer in view of skin permeability and skin irritating property of the medicine. The compounding amount lower than 0.01% by mass tends to make the skin permeability of the medicine insufficient and, on the other hand, the compounding amount higher than 20% by mass tends to generate easily skin irritation.

In the patch of the present invention, preferably the adhesive layer further comprises an absorption enhancer. As an absorption enhancer, any compound conventionally recognized to have an absorption enhancing effect at the skin may be used, including, for example,
(1) fatty acids, aliphatic alcohols, fatty acid amides, and fatty acid ethers having 6 to 20 carbons, which may be saturated or unsaturated, and also may be cyclic, linear, or branched;
(2) aromatic organic acids, aromatic alcohols, and aromatic organic acid esters or ethers; and
(3) lactic acid esters, acetic acid esters, monoterpenes, sesquiterpenes, Azone, Azone derivatives, glycerin fatty acid esters, propylene glycol fatty acid esters, sorbitan fatty acid esters (Span), polysorbates (Tween), polyethylene glycol fatty acid esters, polyoxyethylene hydrogenated castor oils (HCO), polyoxyethylene alkyl ethers, sucrose fatty acid esters and vegetable oils.

Specifically, preferable examples include caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, lauric acid diethanol amide, myristyl myristate, octyldodecyl myristate, cetyl palmitate, methyl salicylate, salicylic acid ethylene glycol, cinnamic acid, methyl cinnamate, cresol, cethyl lactate, lauryl lactate, ethyl acetate, propyl acetate, geraniol, thymol, eugenol, terpineol, L-menthol, borneol, d-limonene, isoeugenol, isoborneol, nerol, dl-camphor, glycerin monocaprirate, glycerin monocaprate, glycerin monolaurate, glycerin monooleate, sorbitan monolaurate, sucrose monolaurate, polysorbate 20, propylene glycol monolaurate, polyethylene glycol monolaurate, polyethylene glycol monostearate, polyoxyethylene oleyl ether, polyoxyethylene lauryl ether, HCO-60, pirotiodecane and olive oil. Among them, oleic acid, lauryl alcohol, myristyl alcohol, oleyl alcohol, isostearyl alcohol, lauric acid diethanol amide, L-menthol, glycerin monocaprirate, glycerin monocaprate, glycerin monooleate, sorbitan monolaurate, propylene glycol monolaurate, polyoxyethylene oleyl ether, polyoxyethylene lauryl ether and pirotiodecane are more preferable, and oleic acid, oleyl alcohol and L-menthol are particularly preferable. In the case where the compounded medicine is an acidic medicine such as diclofenac or a pharmaceutically acceptable salt thereof, the use of oleic acid, oleyl alcohol or L-menthol as the absorption enhancer tends to improve the skin permeability of the medicine, and the use of L-menthol especially tends to improve it.

Such absorption enhancer may be used in combination of two or more kinds, and the combination of oleic acid and L-menthol, or oleyl alcohol and L-menthol is especially preferable. These combinations tend to prominently improve the skin permeability of the medicine. In consideration of sufficient permeability as a patch and irritating properties to the skin such as reddening or edema, the absorption promoter is compounded suitably within a range of 0.01-20% by mass preferably, 0.05-10% by mass more preferably, and 0.1-5% by mass especially preferably based on the total mass of the composition consisting of the adhesive layer.

In the patch of the invention, preferably, the adhesive layer further comprises a solubilizer. Examples of such a solubilizer include liquid fatty acid esters (isopropyl myristate, hexyl laurate, diethyl sebacate, diisopropyl sebacate, and the like), diethylene glycol, triethylene glycol, polyethylene glycol, propylene glycol, dipropylene glycol, triacetin, triethyl citrate and crotamiton. Among them, diethylene glycol, triethylene glycol, polyethylene glycol, propylene glycol and dipropylene glycol are preferable. The use of these solubilizer tends to improve solubility and skin permeability of the medicine, even when a medicine generally having difficulty in satisfying both of solubility and releasability such as diclofenac or a salt thereof is used, and the use of polyethylene glycol tends to especially improve those properties.

When polyethylene glycol is used as a solubilizer, the average molecular weight thereof is preferably 200-20,000, more preferably 400-6,000, especially preferably 1,000-6,000. Polyethylene glycol having the average molecular weight smaller than the smallest limit above described tends to allow the polyethylene glycol and the medicine to react to form an ester pair, causing decrease of the content of the medicine with time. Along with increase of the average molecular weight, the decrease of the medicine content tends to be suppressed sufficiently.

Such solubilizer may be used in combination of two or more kinds. The solubilizer is compounded suitably in a range of 0.5-20% by mass preferably, 1-15% by mass more preferably, and 1-10% by mass especially preferably in total based on the whole composition composing the adhesive layer, while considering sufficient permeability and maintenance of sufficient cohesion force as a patch.

In the patch of the invention, the adhesive layer may further comprise a plasticizer. Examples of such plasticizer include liquid paraffin, petroleum oils (paraffin process oils, naphthen process oils, aromatic process oils, and the like), squalane, squalene, vegetable oils (olive oil, camellia oil, castor oil, tall oil, peanut oil, and the like), silicone oil, dibasic acid ester (dibutyl phthalate, dioctyl phthalate, and the like), liquid rubber (polybutene, liquid isoprene rubber, and the like) and glycol salicylate. Among them, liquid paraffin and liquid polybutene are especially preferable.

Such plasticizer may be used in combination of two or more kinds. The plasticizer is compounded suitably in a range of 5-70% by mass preferably, 10-60% by mass more preferably, and 10-50% by mass especially preferably in total based on the whole composition consisting of the adhesive layer, while considering sufficient permeability and maintenance of sufficient cohesion force as a patch.

In the patch of the invention, the adhesive layer may further comprise an antioxidant, filler, a crosslinker, a preservative, an ultraviolet absorbent or the like if necessary. Desirable examples of such antioxidants include tocopherol and ester derivatives thereof, ascorbic acid, ascorbic acid stearic acid ester, nordihydroguaiaretic acid, dibutylhydroxytoluene (BHT) and butylhydroxyanisole. Desirable examples of such filler include calcium carbonate, magnesium carbonate, silicate (e.g., aluminum silicate, magnesium silicate, and the like), silicic acid, barium sulfate, calcium sulfate, calcium zincate, zinc oxide and titanium oxide. Desirable examples of such crosslinker include thermosetting resins such as amino resin, phenol resin, epoxy resin, alkyd resin and unsaturated polyester, isocyanate compounds, block isocyanate compounds, organic crosslinker, and inorganic crosslinker such as metals and metal compounds. Desirable examples of such preservative include ethyl paraoxybenzoate, propyl paraoxybenzoate and butyl paraoxybenzoate. Desirable examples of such ultraviolet absorbent include p-aminobenzoic acid derivatives, anthranilic acid derivatives, salicylic acid derivatives, coumarin derivatives, amino acid compounds, imidazoline derivatives, pyrimidine derivatives and dioxane derivatives.

Such antioxidants, filler, crosslinkers, preservatives, ultraviolet absorbents are compounded suitably in a range of 10% by mass or less preferably, 5% by mass or less more preferably, and 2% by mass or less especially preferably in total based on the total mass of the composition consisting of the adhesive layer of the patch.

Thickness of the adhesive layer according to the invention (excluding thicknesses of a backing and peelable liner described below), which is prepared by use of the components described above, is preferably 50-300 μm, more preferably 80-200 μm. A thickness lower than 50 μm tends to reduce persistence of an adhesion or adherability and, on the other hand, a thickness more than 300 μm tends to reduce cohesion force or shape preservation property.

As the backing of the transdermal patch of the invention, a backing that does not influence release of the medicine is desirable and stretchable or unstretchable one may be used. Examples of backings usable for the invention include a film, sheet, sheet-shaped porous material, sheet-shaped foam, woven or nonwoven material of synthetic resins such as polyethylene, polypropylene, polybutadiene, ethylene-vinyl acetate copolymer, polyvinylchloride, polyester, nylon and polyurethane, paper, and a laminate thereof.

Next, a preferable example of the production method of the transdermal patch of the invention will be explained. First, respective components (excluding a medicine) consisting of the adhesive layer are mixed with heating at the predetermined ratio under an inactive atmosphere such as nitrogen, the medicine is added, and then the mixture is further stirred to give a homogeneous dissolved composition. Alternatively, aforementioned components and the medicine are added to an organic solvent such as hexane, toluene or ethyl acetate so as to become the predetermined ratio, which is stirred to give a homogeneous dissolved composition.

Next, the dissolved composition is spread directly onto a backing by a usual method, which is covered by a peelable liner and then cut into a desired shape. Or, the dissolved composition may be spread once onto a peelable liner, which is then disposed on a backing to press and transfer the dissolved composition to the backing followed by cutting into a desired shape. On the other hand, when the homogeneous dissolved composition has been obtained by using an organic solvent, preferably it is spread onto a backing followed by drying with a drier to evaporate and remove the organic solvent, which is then covered with a peelable liner; or it is spread onto a peelable liner followed by drying with a drier to evaporate and remove the organic solvent, which is then subjected to press and transfer to a backing.

Examples of such peelable liners include peelable paper, cellophane and synthetic resin films (polyethylene, polypropylene, polyester, polyvinylchloride, polyvinylidene chloride, and the like) having been subjected to a peeling treatment (a treatment for facilitating peeling; e.g., silicone treatment).

The order of compounding each of base components, the medicine and other doping components in the aforementioned production method is described only as an example, and the production method of the patch is not limited to the method of the compounding order.

EXAMPLES

The invention will be explained further specifically on the basis of Examples and Comparative Examples, however the invention is not limited to these Examples and many changes may be possible within the scope of the technical idea of the invention.

Examples 1-9 and Comparative Examples 1-4

Components shown in Table 1 were mixed to toluene to form a mixture, which was stirred to give a homogenous dissolved composition. Next, the dissolved composition was spread onto a peelable liner (polyester film) so as to form a layer having a dried thickness of 100 μm followed by evaporating and removing the toluene with a drier. Then it was disposed on a backing (polyester cloth having a thickness of about 550 μm) to press and transfer the adhesive layer to the backing to give a transdermal patch.

Numerical values of the prescription represented in Table 1 mean "% by mass." As the components listed in Table 1, followings were used.

SIS (styrene-isoprene-styrene block copolymer): manufactured by Japan Synthetic Rubber Co., Ltd., trade name: SIS-5000
PIB (polyisobutylene): manufactured by BASF, trade name: Oppanol B-200
Liquid paraffin: Kaneda Co., Ltd., trade name: Hi-Call M-352
Hydrogenated rosin ester: manufactured by RIKA-Hercules Inc., trade name: Foral 85
Alicyclic petroleum resin: manufactured by ARAKAWA CHEMICAL INDUSTRIES LTD., trade name: ARKON P-100
Polyoxyethylene oleyl ether: manufactured by Nikko Chemicals Co., Ltd., trade name: NIKKOL BO-7

Polyethylene glycol: manufactured by Sanyo Chemical Industries, trade name: Macrogol 4000, average molecular weight: 2600-3800

Example 14: manufactured by Sanyo Chemical Industries, trade name: Macrogol 600, average molecular weight: 570-630

TABLE 1

|  | Ex. 1 | Ex. 2 | Ex. 3 | Ex. 4 | Ex. 5 | Ex. 6 | Ex. 7 | Ex. 8 | Ex. 9 | Comp. Ex. 1 | Comp. Ex. 2 | Comp. Ex. 3 | Comp. Ex. 4 |
|---|---|---|---|---|---|---|---|---|---|---|---|---|---|
| SIS | 15 | 25 | 15 | 10 | 10 | 20 | 25 | 15 | 25 | 15 | 15 | 15 | 10 |
| PIB | 10 | 5 | 5 | 15 | 10 | 15 | 15 | 5 |  | 10 | 5 | 5 | 10 |
| liquid paraffin | 36 | 46 | 41 | 41 | 46 | 36 | 16 | 59 | 31 | 36 | 41 | 36 | 46 |
| hydrogenated rosin ester | 15 | 5 | 20 | 8 | 10 | 15 | 15 | 5 | 8 | 30 |  | 5 | 20 |
| alicyclic petroleum resin | 15 | 10 | 10 | 17 | 15 | 5 | 20 | 10 | 32 |  | 30 | 30 | 5 |
| ammonium chloride | 1 |  | 1 |  | 1 |  | 1 |  |  | 1 | 1 | 1 | 1 |
| diethylamine hydrochloride |  | 1 |  | 1 |  | 1 |  |  | 1 |  |  | 1 |  |
| oleyl alcohol | 3 | 3 |  |  |  | 3 |  |  |  | 3 |  |  |  |
| oleic acid |  |  | 3 | 3 |  |  |  |  |  |  | 3 | 3 |  |
| polyoxyethylene oleyl ether |  |  |  |  | 3 | 3 |  |  |  |  |  |  | 3 |
| dipropylene glycol | 2 |  |  | 2 |  |  |  | 2 |  | 2 |  |  |  |
| triethylene glycol |  |  |  |  | 2 |  |  |  |  |  |  |  | 2 |
| polyethylene glycol |  | 2 | 2 |  |  |  | 2 |  |  |  | 2 | 2 |  |
| crotamiton |  |  |  |  |  | 2 |  |  |  |  |  |  |  |
| Diclofenac sodium | 3 | 3 | 3 | 3 | 3 | 3 | 3 | 3 | 3 | 3 | 3 | 3 | 3 |

Examples 10-11

A transdermal patch was obtained similarly to Example 1 except that components shown in the following prescription were used. Numerical values in the prescription mean "% by mass."

| Prescription of Example 10: | |
|---|---|
| SIS | 15 |
| PIB | 10 |
| Liquid paraffin | 34 |
| Hydrogenated rosin ester | 15 |
| Alicyclic petroleum resin | 15 |
| Ammonium chloride | 1 |
| Oleyl alcohol | 3 |
| L-menthol | 2 |
| Dipropylene glycol | 2 |
| Diclofenac sodium | 3 |
| Prescription of Example 11: | |
| SIS | 15 |
| PIB | 10 |
| Liquid paraffin | 34 |
| Hydrogenated rosin ester | 15 |
| Alicyclic petroleum resin | 15 |
| Ammonium chloride | 1 |
| Oleic acid | 3 |
| L-menthol | 2 |
| Polyethylene glycol | 2 |
| Diclofenac sodium | 3 |

Examples 12-17

Respective transdermal patches were obtained similarly to Example 2 except that the followings were used as polyethylene glycol.

Example 12: manufactured by Sanyo Chemical Industries, trade name: Macrogol 200, average molecular weight: 190-210

Example 13: manufactured by Sanyo Chemical Industries, trade name: Macrogol 400, average molecular weight: 380-420

Example 14: manufactured by Sanyo Chemical Industries, trade name: Macrogol 600, average molecular weight: 570-630

Example 15: manufactured by Sanyo Chemical Industries, trade name: Macrogol 1500, average molecular weight: 1300-1600

Example 16: manufactured by Sanyo Chemical Industries, trade name: Macrogol 4000, average molecular weight: 2600-3800

Example 17: manufactured by Sanyo Chemical Industries, trade name: Macrogol 6000, average molecular weight: 7300-9300

Test Example 1

Adhesive Property Test

Temporal stability of the adhesive force of the transdermal patches obtained in Examples 1, 5, 6 and 8 and Comparative Examples 1 and 4 are evaluated in the following way. Specifically, a patch, which had been left in a temperature-controlled room at 25° C. for 30 min or more in advance, was cut to a size of a test piece holding ring and, after a peelable liner (liner) was peeled off, the adhesive layer was attached to the test piece holding ring while setting its adhesive face downward to place it on a test table. Next, a probe shaft was raised at a constant rate to contact the adhesive face of the patch to a probe made of bakelite having a diameter of 5 mm with a pressure loading of 100 g/cm$^2$ for 1 second. Then, the probe shaft was moved downward again at a rate of 0.5 cm/sec to separate off the probe from the adhesive face, and the force (unit: g/cm$^2$) required at that time was measured as an adhesive force. The measurements of the adhesive force described above were carried out for a patch just produced, and patches preserved for a month at 40° C. or 50° C. to evaluate the stability of adhesive force with time. The results obtained are shown in Table 2.

TABLE 2

|  | Ex. 1 | Ex. 5 | Ex. 6 | Ex. 8 | Comp. Ex. 1 | Comp. Ex. 1 |
|---|---|---|---|---|---|---|
| just produced | 110 | 105 | 95 | 80 | 112 | 101 |
| stored at 40° C. | 107 | 108 | 93 | 79 | 87 | 86 |

TABLE 2-continued

|  | Ex. 1 | Ex. 5 | Ex. 6 | Ex. 8 | Comp. Ex. 1 | Comp. Ex. 1 |
|---|---|---|---|---|---|---|
| for 1 month stored at 50° C. for 1 month | 100 | 103 | 85 | 82 | 44 | 55 |

As is evident from the results shown in Table 2, it was confirmed that the patch of the invention is excellent in the stability of the adhesive force with time and, on the other hand, patches comprising no or a little amount of petroleum resin as a tackifier are poor in the stability of the adhesive force with time.

Test Example 2

Medicine Solubility Test

The medicine solubility (medicine crystallization) of the transdermal patches obtained in Examples 2, 3, 7 and 9 and Comparative Examples 2 and 3 were evaluated as follows. That is, the patches were preserved in a thermo-hygrostat of 25° C. and 60% for a month, and then crystallization of the medicine in the adhesive layer was observed and evaluated according to the following criteria:
x crystal separation;
Δ crystal was observed slightly;
o no crystal separation.
The obtained results are shown in Table 3.

TABLE 3

|  | crystallization |
|---|---|
| Example 2 | o |
| Example 3 | o |
| Example 7 | o |
| Example 9 | o |
| Comparative Example 2 | x |
| Comparative Example 3 | Δ |

As is evident from the results shown in Table 3, it was confirmed that the patch of the invention is excellent in the medicine solubility and, on the other hand, patches comprising no or a little amount of rosin-based resin as a tackifier are poor in the medicine solubility.

Test Example 3

In vitro Medicine Skin Permeability Test

The medicine skin permeability of the transdermal patches obtained in Examples 1, 4, 5, 10 and 11 and Comparative Examples 1 and 4 were evaluated as follows. That is, after extirpating dorsal skin of a hairless mouse (8 weeks old, female), fat on a dermis side was removed carefully, which was set to a flow-through-cell, whose periphery of a receptor layer was circulated with water of 37° C., so that the dermis side became a receptor layer side. A patch was attached to the horny layer side. Phosphate buffer, pH 7.4, was supplied to the receptor layer, and sampling was carried out at a speed of 1 ml/hour every 4 hours up to 24 hours. As regarding respective solutions obtained at respective times, the flow volume was measured precisely, the medicine concentration was measured by high performance liquid chromatography, permeability rate for 4 hours was calculated, and skin permeability rate at the steady state was determined according to the following formula. The obtained results are shown in FIGS. 2 and 3.

$$\text{Skin permeability rate } (\mu g/cm^2/hr) = [\text{Sample Concentration } (\mu g/ml) \times \text{Flow volume}(ml)]/\text{preparation-applied area } (cm^2) \times 4 \text{ hr}$$

Figure 2:
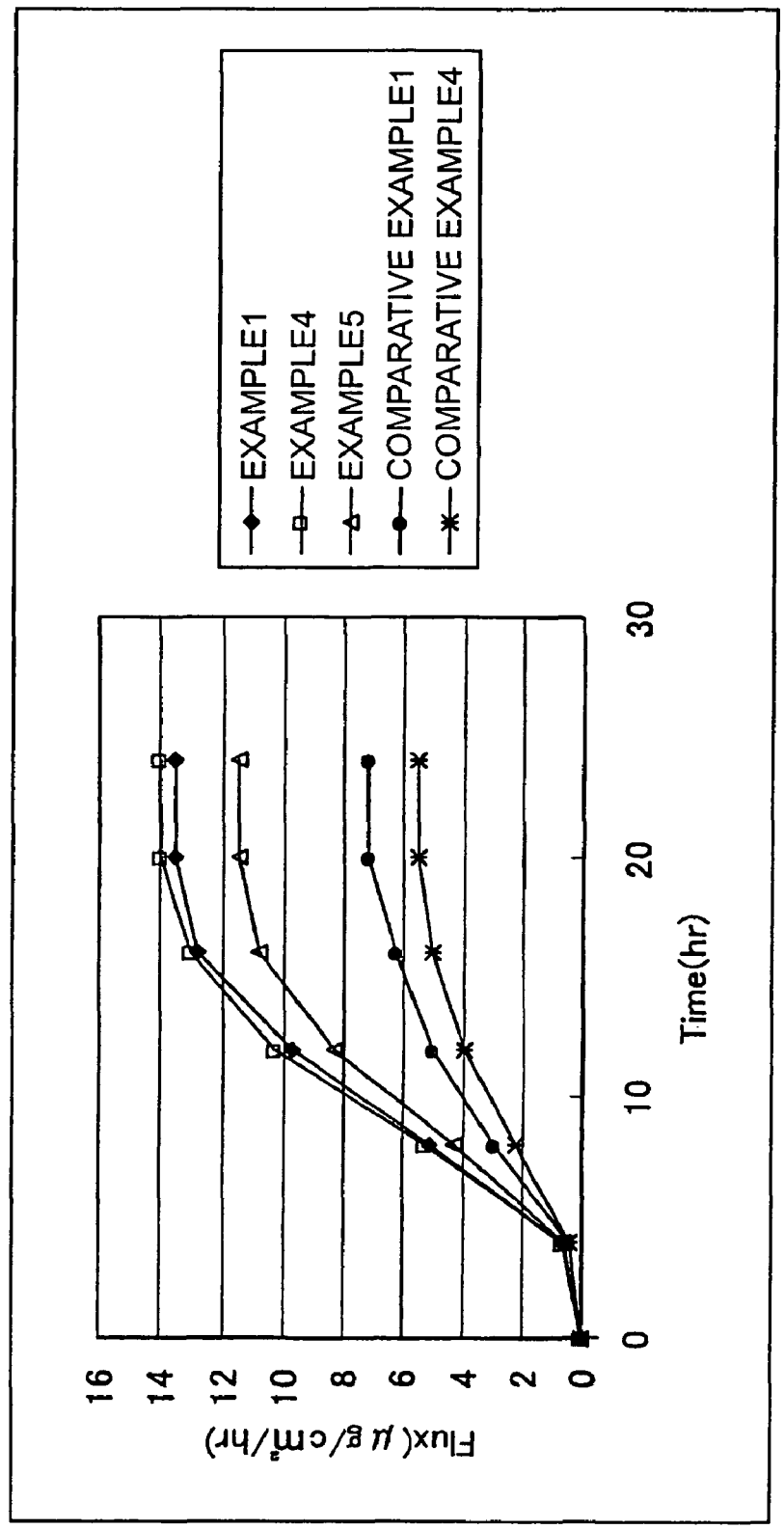
FIG. 2 is a graph exhibiting the results of medicine releasability tests in Examples 1, 4 and 5 and Comparative Examples 1 and 4.

As is evident from the results shown in FIG. 2, it was confirmed that the patch of the invention is excellent in the medicine releasability and, on the other hand, patches comprising no or a little amount of petroleum resin as a tackifier are poor in the medicine releasability.

Figure 3:
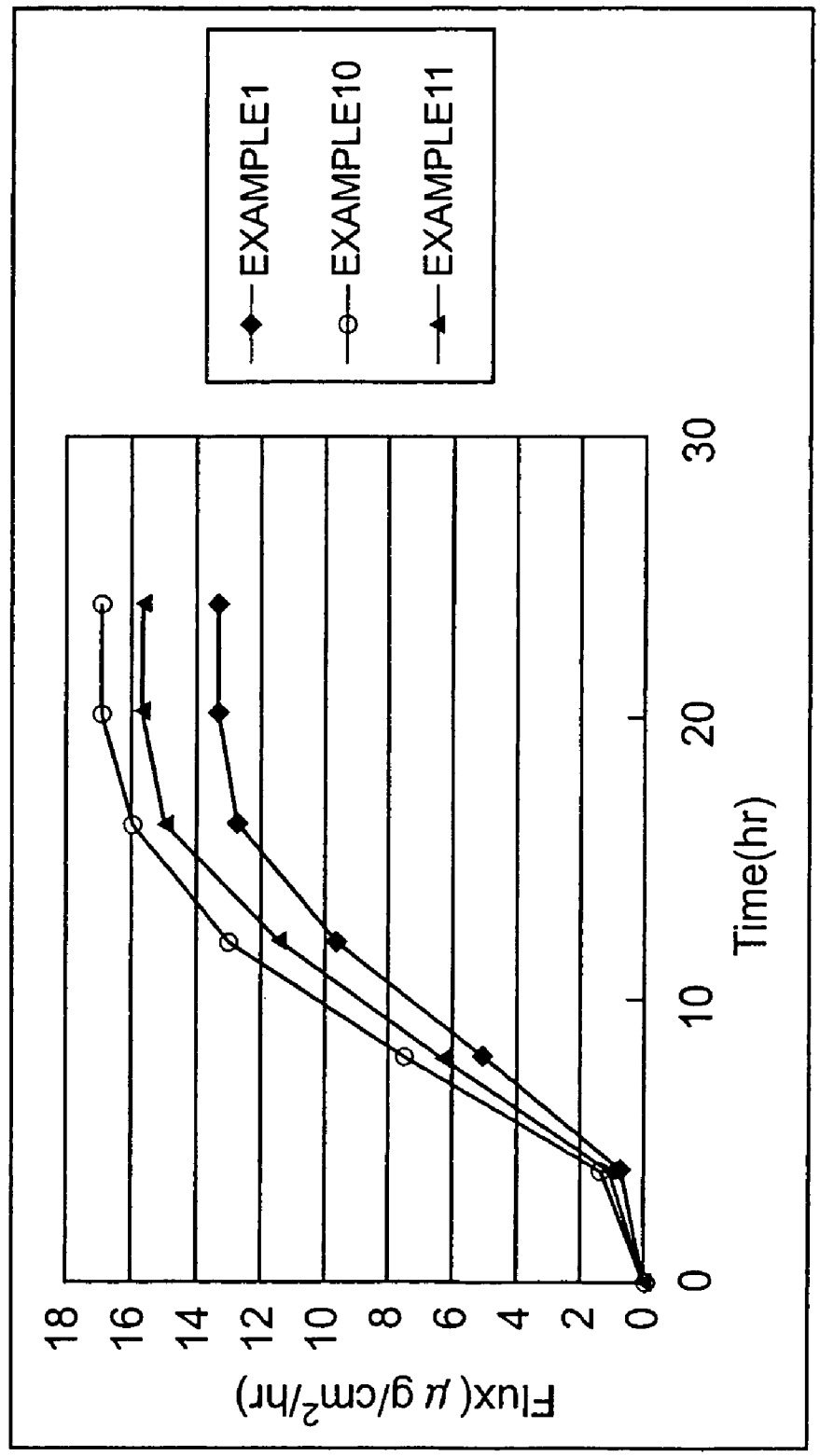
FIG. 3 is a graph exhibiting the results of medicine releasability tests in Examples 1, 10 and 11.

Further, as is evident from the results shown in FIG. 3, it was confirmed that use of the combination of oleyl alcohol and L-menthol (Example 10) or oleic acid and L-menthol (Example 11) especially improves skin permeability of the medicine.

Test Example 4

Medicine Stability Test

The medicine stability of transdermal patches obtained in Examples 12-17 was evaluated as follows. That is, the patches were preserved for 2 months, 3 months or 6 months at 40° C. or for 2 months at 50° C., then remained amount of the medicine (diclofenac) in the patches after preservation was measured by liquid chromatography to calculate the medicine remaining ratio (%). The measurement was repeated three times, and the average of the obtained results is shown in Table 4.

TABLE 4

|  | 40° C. for 2 months | 40° C. for 3 months | 40° C. for 6 months | 50° C. for 2 months |
|---|---|---|---|---|
| Ex. 12 | 94.0 | 93.2 | 88.1 | 89.3 |
| Ex. 13 | 95.2 | 94.7 | 90.2 | 90.2 |
| Ex. 14 | 96.1 | 95.3 | 90.3 | 90.5 |
| Ex. 15 | 99.2 | 98.5 | 97.5 | 97.3 |
| Ex. 16 | 98.9 | 98.8 | 98.2 | 98.0 |
| Ex. 17 | 99.0 | 99.0 | 98.2 | 98.1 |

As is evident from the results shown in Table 4, it was confirmed that along with increase of the average molecular weight of polyethylene glycol, the reduction of medicine content is sufficiently suppressed.

Industrial Applicability

As described above, according to the invention, even when a medicine generally having difficulty in satisfying both of solubility and releasability such as diclofenac or a salt thereof is used as the medicine, it becomes possible to obtain a transdermal patch achieving both of sufficient solubility of the medicament and sufficient releasability of the medicine with a good balance in a high level and, in addition, having an excellent temporal stability of the adhesive force.

The invention claimed is:
1. A transdermal patch, comprising:
a backing; and
an adhesive layer laminated on the backing, the adhesive layer comprising
a tackifier present in an amount of 15% to 50% by mass of the adhesive layer, the tackifier comprising
a rosin-based resin present in an amount, and
a petroleum resin present in an amount,
the said amount of petroleum resin present being ⅓ to 4 times the said amount of rosin-based resin by mass, diclofenac sodium present in an amount of 0.1-40% by mass of the adhesive layer, and polyethylene glycol present in an amount of 1-10% by mass of the adhesive layer, wherein the polyethylene glycol has an average molecular weight in a range selected from the group consisting of 1300-1600, 2600-3800 and 7300-9300.

2. The transdermal patch according to claim 1, wherein the rosin-based resin is hydrogenated rosin ester.

3. The transdermal patch according to claim 1, wherein the petroleum resin is one or more resins selected from the group consisting of alicyclic petroleum resin and hydrogenated alicyclic petroleum resin.

4. The transdermal patch according to claim 1, wherein the adhesive layer further comprises L-menthol.

* * * * *